US012275763B2

(12) United States Patent
Liu et al.

(10) Patent No.: US 12,275,763 B2
(45) Date of Patent: Apr. 15, 2025

(54) RamA TRANSCRIPTION FACTOR MUTANT FOR PROMOTING PRODUCTION OF N-ACETYLGLUCOSAMINE AND USE THEREOF (71) Applicants: JIANGNAN UNIVERSITY, Wuxi (CN); SHANDONG RUNDE BIOTECHNOLOGY CO., LTD., Taian (CN)

(72) Inventors: Long Liu, Wuxi (CN); Jian Chen, Wuxi (CN); Xueqin Lv, Wuxi (CN); Jianxing Lu, Taian (CN); Changfeng Liu, Taian (CN); Guocheng Du, Wuxi (CN); Jianghua Li, Wuxi (CN); Chen Deng, Taian (CN); Jiangong Lu, Taian (CN)

(73) Assignees: JIANGNAN UNIVERSITY, Wuxi (CN); SHANDONG RUNDE BIOTECHNOLOGY CO., LTD., Taian (CN)

( * ) Notice: Subject to any disclaimer, the term of this patent is extended or adjusted under 35 U.S.C. 154(b) by 1067 days.

(21) Appl. No.: 17/276,235

(22) PCT Filed: Jan. 7, 2020

(86) PCT No.: PCT/CN2020/070602
§ 371 (c)(1),
(2) Date: Mar. 15, 2021

(87) PCT Pub. No.: WO2021/128465
PCT Pub. Date: Jul. 1, 2021

(65) Prior Publication Data
US 2022/0106366 A1 Apr. 7, 2022

(30) Foreign Application Priority Data
Dec. 26, 2019 (CN) .......................... 201911361421.6

(51) Int. Cl.
C07K 14/34 (2006.01)
C12N 1/20 (2006.01)
C12N 15/77 (2006.01)
C12P 19/26 (2006.01)
C12R 1/15 (2006.01)

(52) U.S. Cl.
CPC .............. C07K 14/34 (2013.01); C12N 1/205 (2021.05); C12N 15/77 (2013.01); C12P 19/26 (2013.01); C12R 2001/15 (2021.05)

(58) Field of Classification Search
None
See application file for complete search history.

(56) References Cited

U.S. PATENT DOCUMENTS

2006/0228712 A1   10/2006   Nakagawa et al.

FOREIGN PATENT DOCUMENTS

CN    108424870 A       8/2018
EP      3521305 A1      8/2019
WO  WO2019154679 A1 *   8/2019

OTHER PUBLICATIONS

Shah, A. et al "The RamA regulon: complex regulatory interactions in relation to central metabolism in Corynebacterium glutamicum". Applied Microbiology and Biotechnology, vol. 102 (2018), pp. 5901-5910 (Year: 2018).*
Graf, M. et al. "Continuous adaptive evolution of fast-growing Corynebacterium glutamicum strain independent of protocatechuate". Frontiers in Microbiology, vol. 10 (Aug. 2019), pp. 1648 (Year: 2019).*
Deng, C. et al. "Synergistic improvement of N-acetylglucosamine production by engineering transcription factors and balancing redox cofactors". Metabolic Engineering, vol. 67 (2021), pp. 330-346 (Year: 2021).*
Liu, L. et al. "Microbial production of glucosamine and N-acetylglucosamine: advances and perspectives". Applied Microbiological Biotechnology, vol. 97 (2013), pp. 6149-6158 (Year: 2013).*
Kataoka, N. et al. " Engineering of Corynebacterium glutamicum as a prototrophic pyruvate-producing strain: characterization of a ramA-deficient mutant and its application for metabolic engineering". Bioscience, Biotechnology, and Biochemistry, vol. 83, No. 2 (2019), pp. 372-380 (Year: 2019).*
Deng, C. et al. "Metabolic engineering of Corynebacterium glutamicum S9114 based on whole-genome sequencing for efficient N-acetylglucosamine synthesis". Synthetic and Systems Biotechnology, vol. 4 (2019), pp. 120-129 (Year: 2019).*

(Continued)

Primary Examiner — Anna Skibinsky
Assistant Examiner — Alexandra Geraldine Dace Denito
(74) Attorney, Agent, or Firm — SZDC Law PC (57) ABSTRACT The present invention discloses a RamA transcription factor mutant for promoting the production of N-acetylglucosamine and use thereof. The mutant is obtained by mutating lysine at position 90 to asparagine and serine at position 92 to lysine in a parent having an amino acid sequence as shown in SEQ ID NO: 2. The present invention provides a genetically engineered strain that overexpresses the RamA transcription factor mutant and increases the production of N-acetylglucosamine. By overexpressing the transcription factor RamA that is involved in the regulation of carbon metabolism, the extracellular accumulation of N-acetylglucosamine is increased, with a maximum concentration reaching 31.5 g/L, which lays a foundation for further metabolic engineering of *Corynebacterium glutamicum* to produce glucosamine. The method for constructing recombinant *Corynebacterium glutamicum* of the invention is simple, and convenient in use, and thus has good application prospects.

8 Claims, 2 Drawing Sheets
Specification includes a Sequence Listing.

(56) References Cited

OTHER PUBLICATIONS

Zhihao Wang et al., "Alterations in the transcription factors GntR1 and RamA enhance the growth and central metabolism of Corynebacterium glutamicum," Metabolic Engineering, No. 48 (May 9, 2018).

Michaela Graf et al., "Continuous adaptive evolution of a fast-growing Corynebacterium glutamicum strain independent of protocatechuate," Frontiers in Microbiology, vol. 10 (Aug. 6, 2019).

* cited by examiner

RamA TRANSCRIPTION FACTOR MUTANT FOR PROMOTING PRODUCTION OF N-ACETYLGLUCOSAMINE AND USE THEREOF

This application is the National Stage Application of PCT/CN2020/070602, filed on Jan. 7, 2020, which claims priority to Chinese Patent Application No. 201911361421.6, filed on Dec. 26, 2019, which is incorporated by reference for all purposes as if fully set forth herein.

FIELD OF THE INVENTION

The present invention relates to the technical field of metabolic engineering, and more particularly to a RamA transcription factor mutant for promoting the production of N-acetylglucosamine and use thereof.

DESCRIPTION OF THE RELATED ART

N-acetylglucosamine (GlcNAc) is a derivative of glucosamine. It is reductive and also an important precursor for the synthesis of bifidus factor and hyaluronic acid. N-acetylglucosamine is also referred to as 2-(acetylamino)-2-deoxyglucose or N-acetylaminoglucose, and is a basic unit constituting a variety of polysaccharides, and has important physiological functions in the body. *Corynebacterium glutamicum* is a gram-positive soil bacterium with high GC content from the Actinobacteria. It has been used in the industrial production of amino acids and is designed to produce various compounds, including polymer building blocks and biofuels. Since the initial publication of the genome sequence, the multifunctional metabolic pathway, the genetic component and the regulatory mechanism in *Corynebacterium glutamicum* have been researched extensively. In order to improve the production efficiency by biotechnologies, genetic tools and omics-based analysis methods, including transcriptomics, proteomics, metabolomics and rheology, are developed based on the genome sequence information and are widely used to study the metabolic pathways and its post-transcriptional regulation.

In the previous research, to increase the expression of a target gene in *Corynebacterium glutamicum*, genome engineering, optimization of promoter and RBS sequences, use of site-directed mutagenesis, transformation of transport systems and the like are often used by the scholars. To truthfully realize the qualitative modification of engineered strains and the rational design of cell engineering, the interaction between any two of gene expression, transcription regulation and metabolic reactions need to be comprehensively considered, starting from the cell and system as a whole.

SUMMARY OF THE INVENTION

To solve the above technical problems, the present invention provides a RamA transcription factor mutant for promoting the production of N-acetylglucosamine, so that the carbon metabolic flux in *Corynebacterium glutamicum* flows more to the production of N-acetylglucosamine, thereby improving the ability of *Corynebacterium glutamicum* to produce N-acetylglucosamine. This is of great economic value and social significance.

A first object of the present invention is to provide a RamA transcription factor mutant for promoting the production of N-acetylglucosamine. The mutant is obtained by mutating lysine at position 90 to asparagine and serine at position 92 to lysine in a parent having an amino acid sequence as shown in SEQ ID NO: 2.

Preferably, the nucleotide sequence of the parent is as shown in SEQ ID NO: 1.

Preferably, the amino acid sequence of the RamA transcription factor mutant is as shown in SEQ ID NO: 4.

Preferably, the nucleotide sequence of the RamA transcription factor mutant is as shown in SEQ ID NO: 3.

A second object of the present invention is to provide a genetically engineered strain with increased production of N-acetylglucosamine. The genetically engineered strain is obtained by over-expressing a RamA transcription factor mutant using *Corynebacterium glutamicum* as a host strain.

Preferably, the host strain is *Corynebacterium glutamicum* S9114ΔnagA-ΔgamA-Δldh.

Preferably, the genetically engineered strain uses pTYW-4-ceN-C·glglmS as an expression vector. The specific construction process of the expression vector pTYW-4-ceN-C·glglmS is as described in Chen Deng, Xueqin Lv, Yanfeng Liu, Long Liu. Metabolic engineering of *Corynebacterium glutamicum* S9114 based on whole-genome sequencing for efficient N-acetylglucosamine synthesis. Synthetic and Systems Biotechnology, 2019. 4: 120-129.

A third object of the present invention is to provide a method for constructing the genetically engineered strain, which includes the following steps:
(1) ligating a coding gene of the RamA transcription factor mutant to the expression vector pTYW-4-ceN-C·glglmS, to construct a pTYW-4-ceN-C·glglmS-RamA vector; and
2) transforming the vector constructed in Step (1) into a host strain *Corynebacterium glutamicum* S9114ΔnagA-ΔgamA-Δldh, to obtain the genetically engineered strain.

A fourth object of the present invention is to provide use of the RamA transcription factor mutant or the genetically engineered strain in the production of N-acetylglucosamine.

Preferably, the genetically engineered strain is inoculated into a fermentation medium, and undergoing aerated fermentation for 72-100 h at 28-30° C.

Preferably, the fermentation medium comprises glucose 90-110 g/L, corn steep liquor 8-12 g/L, $KH_2PO_4$ 0.8-1.2 g/L, $(NH_4)_2SO_4$ 18-22 g/L, $MgSO_4$ 0.4-0.6 g/L, $CaCO_3$ 18-22 g/L, and $FeSO_4$ 0.16-0.20 g/L.

The present invention has the following beneficial effects: The present invention provides a RamA transcription factor mutant for promoting the production of N-acetylglucosamine, and provides a genetically engineered strain that overexpresses the RamA transcription factor mutant and can increase the production of N-acetylglucosamine. By overexpressing the transcription factor RamA that is involved in the regulation of carbon metabolism, the extracellular accumulation of N-acetylglucosamine is increased, with a maximum concentration reaching 31.5 g/L, which lays a foundation for further metabolic engineering of *Corynebacterium glutamicum* to produce glucosamine. The method for constructing recombinant *Corynebacterium glutamicum* provided in the invention is simple, and convenient in use, thus having good application prospects.

DETAILED DESCRIPTION OF THE PREFERRED EMBODIMENTS

The present invention will be further described below with reference to the accompanying drawings and specific examples, so that those skilled in the art can better understand and implement the present invention; however, the present invention is not limited thereto.

Determination Method of N-Acetylglucosamine:

High performance liquid chromatography (HPLC): AGILENT® 1260, RID detector, HPX-87H column (Bio-Rad Hercules, CA), mobile phase: 5 mM $H_2SO_4$, flow rate 0.6 mL/min, column temperature 35° C., injection volume 10 µL.

Liquid seed activation medium (LBG) (g/L): peptone 10.0, yeast extract 5.0, NaCl 10.0, glucose 5.0, where the filling volume is 20 ml per 250 ml Erlenmeyer flask.

Solid seed activation medium (LBG solid) (g/L): peptone 10.0, powdery yeast 5.0, NaCl 10.0, glucose 5.0, nutrient agar 15.0-20.0.

Competent medium (g/L): peptone 10.0, yeast extract 5.0, NaCl 10.0, glycine 30.0, isoniazid 4.0, and 10 ml of Tween 80, where the filling volume is 50 ml per 500 ml Erlenmeyer flask.

Recovery medium after electroporation LBHIS (g/L): peptone 5.0, yeast extract 2.5, NaCl 5.0, brain heart infusion 18.5, sorbitol 91.0.

Solid medium for transformant detection (g/L): peptone 5.0, yeast extract 2.5, NaCl 5.0, brain heart infusion 18.5, sorbitol 91.0, nutrient agar 15.0-20.0.

Seed culture medium (g/L): glucose 25.0, corn steep liquor 20.0, $KH_2PO_4$ 1.0, $(NH_4)_2SO_4$ 0.5, urea 1.25, pH 7.0.

Fermentation medium (g/L): glucose 40.0, corn steep liquor 20.0, $KH_2PO_4$ 1.0, $(NH_4)_2SO_4$ 20.0, $MgSO_4$ 0.5, $CaCO_3$ 20.0, pH 7.0.

Optimized fermentation medium (g/L): glucose 100.0, corn steep liquor 10.0, $KH_2PO_4$ 1.0, $(NH_4)_2SO_4$ 20.0, $MgSO_4$ 0.5, $CaCO_3$ 20.0, $FeSO_4$ 0.18, pH 7.0.

Sterilization conditions: 115° C., 20 min. 25 mg/L kanamycin sulfate is added to all media for transformant detection or recombinant culture.

Example 1: Construction of Recombinant Plasmid pTYW-4-ceN-C·glglmS-RamA (1) Amplification primers were designed according to the genome of S9114 to amplify the RamA gene.

```
Upstream primer FragmentRamA.FOR
(SEQ ID NO: 5):
5'-CGTCGAATAAGACGCGCCCTATGGGT-3'

Downstream primer FragmentRamA.REV
(SEQ ID NO: 6):
5'-CCTTTGCTAGTTTAAGGCAGTGCGCCGAT-3'
```

Primers for linearization of the vector pTYW-4-ceN-C·glglmS were also designed.

```
Upstream primer VectorRamA.FOR
(SEQ ID NO: 7):
5'-CACTGCCTTAAACTAGCAAAGGAGAA
GAAAAGCCGGA-3'

Downstream primer VectorRamA.REV
(SEQ ID NO: 8):
5'-TAGGGCGCGTCTTATTCGACGGTGAC
AGACTTTGCCAGGTTACGAG-3'
```

Primers FragmentRamA·FOR and FragmentRamA·REV were used, and the laboratory-preserved *Corynebacterium glutamicum* S9114 was used as a template. PCR conditions: pre-denaturation at 95° C. for 10 min; 30 cycles of denaturation at 98° C. for 1 min, annealing at 55° C. for 1 min, and extension at 72° C. for 1 min; and final extension at 72° C. for 10 min. The PCR product was recovered with a DNA purification kit. The RamA gene was amplified from the genome of *Corynebacterium glutamicum* S9114, and the RamA gene was amplified using LA Taq HS DNA polymerase.

The plasmid pTYW-4-ceN-C·glglmS previously constructed in the laboratory was used as an expression vector to express the RamA gene, and the specific construction process of pTYW-4-ceN-C·glglmS plasmid was as described in Chen Deng, Xueqin Lv, Yanfeng Liu, Long Liu. Metabolic engineering of *Corynebacterium glutamicum* S9114 based on whole-genome sequencing for efficient N-acetylglucosamine synthesis. Synthetic and Systems Biotechnology, 2019. 4: 120-129.

Primers VectorRamA·FOR and VectorRamA·REV were used, and the extracted plasmid pTYW-4-ceN-C·glglmS was used as a template. PCR conditions: pre-denaturation at 95° C. for 3 min; 30 cycles of denaturation at 98° C. for 1 min, annealing at 55° C. for 1 min, and extension at 72° C. for 5 min; and final extension at 72° C. for 10 min. The PCR product was recovered with a DNA purification kit to obtain the linearized plasmid pTYW-4-ceN-C·glglmS.

(2) The CLONEXPRESS® II One Step Cloning Kit from Vazyme Biotech Co., Ltd. was used for ligation. The linearized vector obtained by PCR and the target gene fragment carrying a homologous end of the vector were mixed at a molar ratio of 3:1 after extraction, 4 µL of 5×CE II Buffer and 2 µL of Exnase II were added, and then ddH$_2$O was added to give a total volume of the ligation system of 20 µL. The system was reacted at 37° C. for 30 min, and allowed to stand at 4° C. after cooling. Then 10 µL of the ligation system was transformed into *E. coli*. BL21 (DE3) competent cells (see the instruction of Takara Preparation Kit for Competent *Escherichia coli*). The transformants confirmed to be correct by colony PCR were selected, sent to GENEWIZ and verified by sequencing, to obtain the recombinant expression vector pTYW-4-ceN-C·glglmS-RamA.

The plasmid pTYW-4-ceN-C·glglmS-RamA was transformed into *Corynebacterium glutamicum* strain 59114ΔnagA-ΔgamA-Δldh by electroporation.

Preparation of Electroporation-Competent *Corynebacterium glutamicum*:

(1) *C. glutamicum* was inoculated onto LBG medium (where the cells needed to be picked up from a fresh slant culture, otherwise the growth of the bacteria would be affected), placed on a traveling shaker (200 rpm), and incubated at 30° C. for 16 h until $OD_{562}$ reached 3.0.

(2) 10% was inoculated into a competent medium to allow for an $OD_{562}$ of 0.3, placed on a traveling shaker (200 rpm), and incubated at 30° C. until $OD_{562}$ reached 0.9 (where the incubation time was about 3-5 h, and the cells were in a logarithmic growth phase at this time; and the subsequent operations could also be performed if the $OD_{562}$ of the cell suspension was persistently to be low as about 0.6). The concentration of the cells needed to be ensured to be as high as possible, and the concentration factor was generally 100 times (where 50 mL competent medium was concentrated to 0.5 mL to prepare 5 tubes of competent cells).

(3) The cell suspension was allowed to stand in an ice water bath for 15 min and then centrifuged at 4,000 rpm and 4° C. for 10 min, and the supernatant was discarded carefully.

(4) The cells were fully suspended in 30 mL of pre-cooled 10% glycerol and then centrifuged at 4,000 rpm and 4° C. for 10 min, and the supernatant was discarded carefully. The cells were repeatedly washed 4 times.

(5) The cells (concentrated 100 times) were re-suspended in 500 μL of pre-cooled 10% glycerol, and filled in 1.5 mL sterile centrifuge tubes in an amount of 100 μL per tube.

(6) The cells were stored at −80° C. for later use. To ensure the transformation efficiency of competent cells, the cells are preferred to be used immediately after preparation. The cells should not be left for more than 1 week, otherwise the cell content will be released due to the lysis of competent cells, which causes the breakdown of electroporation cuvette during the subsequent electroporation and affects the transformation efficiency.

Electroporation of *Corynebacterium glutamicum*

(1) Competent *Corynebacterium glutamicum* stored at −80° C. were thawed in an ice bath.

(2) 1-5.0 μL of plasmid was added and mixed well (where the total amount of DNA was about 1.0 μg), and allowed to stand in an ice bath for 5-10 min.

(3) The system was added into a pre-cooled 0.1 cm electroporation cuvette and subjected to 2 electric shocks at 1.8 KV for 5 ms each.

(4) 1.0 mL of preheated recovery medium (LBWS) was quickly added, mixed well and transferred to a new 1.5 mL sterile centrifuge tube. The system was allowed to stand in a water bath at 46° C. for 6 min, and then stand in an ice bath.

(5) The cells were placed on a traveling shaker (100 rpm) and incubated at 30° C. for 2 h.

(6) The cells were centrifuged for 1 min at 6,000 rpm and normal temperature, coated onto a detection plate of corresponding resistant transformant, and incubated in an incubator at a constant temperature of 30° C. for 2-3 days.

(7) Efficiency verification of competent cells: 5.0 μL of sterile ddH$_2$O was added as a negative control, and no colonies were grown. For the positive control, 1-5 μL of the plasmid pXMJ19 (where the total DNA content was about 1.0 μg) was added, and a large number of colonies were grown.

Example 2: Construction of RamA Gene Mutant Library in Recombinant *Corynebacterium glutamicum*

Construction Method of RamA Gene Mutant Library:

The recombinant plasmid pTYW-4-ceN-C·glglmS-RamA was used as a template, and the primers used were:

```
Upstream primer RamAM.FOR
(SEQ ID NO: 9):
5'-NNNGATNNNGCGATTCAGGATGAGGGC-3'

Downstream primer RamAM.REV
(SEQ ID NO: 10):
5'-CTCATGTGAAATGACATTTGCCCTGGTGT

AATCAC-3'
```

The primers were 5'-phosphorylated with a phosphorylation kit. Then the 5'-phosphorylated primers were used for a PCR procedure including pre-denaturation at 95° C. for 3 min; 30 cycles of denaturation at 98° C. for 1 min; annealing at 55° C. for 1 min and extension at 72° C. for 5 min; and final extension at 72° C. for 10 min. The PCR product was recovered with a DNA purification kit to obtain a series of linearized plasmids pTYW-4-ceN-C·glglmS-RamA$^M$ containing a mutant site.

The PCR product obtained was purified, and the plasmid template was digested with DpnI endonuclease for 2 h. 15 μL of the digested product was taken and ligated with T4 ligase at 16° C. for 1 h or overnight. The reaction system was: PCR product of linearized plasmid 15 μL, T4 DNA Ligase Buffer (10×)*2 μl, T4 DNA Ligase 1 μl, and ddH$_2$O 2 μl. Then, the ligated product was recovered by an extraction kit, and directly transformed into the host strain *Corynebacterium glutamicum* S9114ΔnagA-ΔgamA-Δldh, to obtain *Corynebacterium glutamicum* containing a RamA gene mutant library. The obtained RamA gene mutants all carry two mutant sites that are 90K and 92S respectively. Amino acids at the two sites were randomly mutated into any combination of amino acids.

Example 3: Over-Expression of RamA Gene in Recombinant *Corynebacterium glutamicum* and Effect of RamA$^M$ Gene on N-Acetylglucosamine Production High-Throughput Screening Method for Mutant Library:

Firstly, the mutated colony grown on the coated plate were inoculated into a shallow 48-well plate and used as a seed culture (where 6 plates were inoculated, each of which was inoculated with 46 mutant strains and 2 control strains, and a total of 276 mutant strains and 12 control strains were included). After culturing at 37° C. for 10 h, 2 μL was transferred to a screening medium in a deep 48-well plate, and cultured by fermentation for 48 h. After fermentation, the culture was centrifuged and 2 μL of the supernatant was transferred to a 96-well PCR plate. 43 μL of ultrapure water and 1 μL of potassium tetraborate solution (1.5 g potassium tetraborate dissolved in 25 mL of ultrapure water) were added, and then heated in a metal bath at 96° C. for 5 minutes. Then, the reaction was terminated. 10 μL of the reaction solution was transferred to a shallow 96-well plate, and then 125 μL of a PDABA solution (1 g of p-dimethylbenzaldehyde dissolved in 100 mL of glacial acetic acid containing 1.25% hydrochloric acid) was added, and reacted at 37° C. on a shaker for 10 min. The absorbance at A585 was measured on a microplate reader, and the absorbance was positively correlated with the content of GlcNAc. According to the data measured by the microplate reader, the mutant strain corresponding to the highest production in the shallow 96-well plate was found, which was used as a starting strain for the next round of culture. After multiple rounds of screening, the high-production strains obtained in the final preliminary screening were verified by shake-flask culture.

The preliminarily screened strain obtained after high-throughput screening on the plate were inoculated into a shake flask and re-screened and verified by fermentation.

In one embodiment of the present invention, the fermentation was carried out as follows: the seed cultured at 28-30° C. and 220 rpm for 16 h was transferred to the fermentation medium in an amount such that the initial $OD_{562}$ of the fermentation medium was 1.6, and cultured for 72-100 h at 28-30° C. and 220 rpm. The production of GlcNAc was determined by HPLC.

Figure 1:
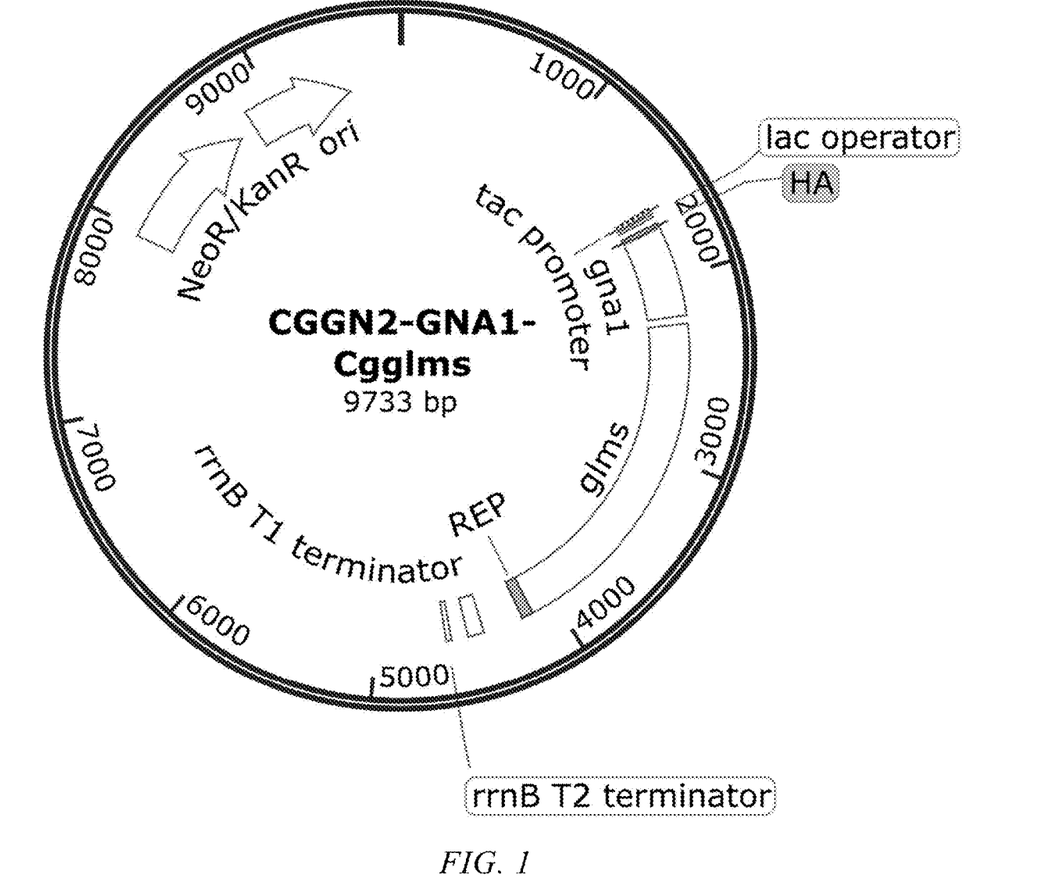
FIG. 1 shows the map of pTYW-4-ceN-C·glglmS plasmid.
Figure 2:
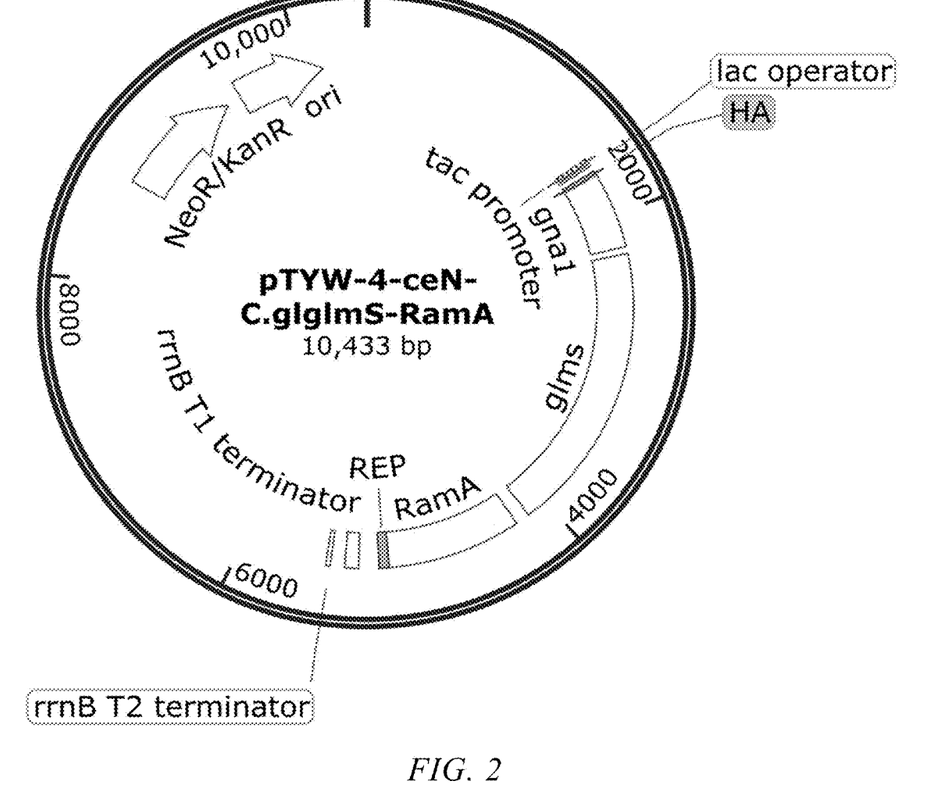
FIG. 2 shows the map of the constructed recombinant pTYW-4-ceN-C·glglmS-RamA plasmid.
Figure 3:
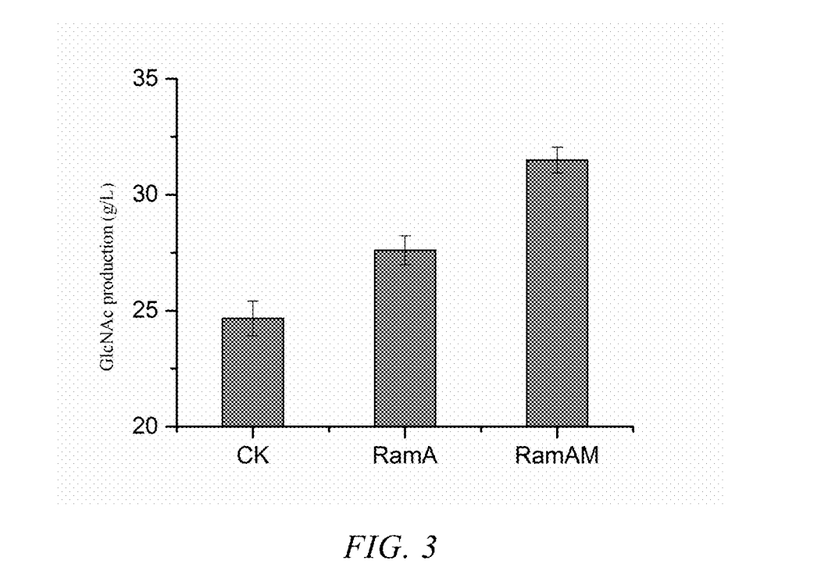
FIG. 3 shows the GlcNAc production in supernatants of shake flask fermentation with different strains.

The recombinant strain containing plasmid pTYW-4-ceN-C·glglmS was used as a control, cultured and fermented under the same conditions. The GlcNAc production was 24.7 g/L after 72 h, and the GlcNAc production by the strain containing the plasmid pTYW-4-ceN-C·glglmS-RamA overexpressing the RamA gene was 27.6 g/L after 72 h (FIG. 3). After the strains in the mutant library were preliminarily screened in the plate and re-screened in a shake flask, finally a strain with the highest GlcNAc production was obtained. After 2 h, the GlcNAc production was 31.5 g/L (FIG. 3). The plasmid carried by the mutant strain was named pTYW-4-ceN-C·glglmS-RamA$^M$. Primers were designed to amplify the mutant nucleotide sequence of the plasmid, and the mutant nucleotide sequence was sent to GENEWIZ for sequencing. The mutant gene RamA$^M$ carries two mutant sites, namely K90N and S92K.

The above-described embodiments are merely preferred embodiments for the purpose of fully illustrating the present invention, and the scope of the present invention is not limited thereto. Equivalent substitutions or modifications can be made by those skilled in the art based on the present invention, which are within the scope of the present invention as defined by the claims.

What is claimed is:

1. A RamA transcription factor mutant for promoting the production of N-acetylglucosamine, wherein the nucleotide sequence of the RamA transcription factor mutant comprises SEQ ID NO: 3.

2. A genetically engineered strain with increased production of N-acetylglucosamine, wherein the genetically engineered strain is obtained by over-expressing the RamA transcription factor mutant according to claim 1 using *Corynebacterium glutamicum* as a host strain.

3. The genetically engineered strain according to claim 2, wherein the host strain is *Corynebacterium glutamicum* S9114ΔnagA-ΔgamA-Δldh.

4. The genetically engineered strain according to claim 2, wherein the genetically engineered strain uses pTYW-4-ceN-C·glglmS as an expression vector.

5. A method for constructing a genetically engineered strain according to claim 2, comprising steps of
   (1) ligating a coding gene of the RamA transcription factor mutant to the expression vector pTYW-4-ceN-C·glglmS, to construct a pTYW-4-ceN-C·glglmS-RamA vector; and
   (2) transforming the vector constructed in Step (1) into a host strain *Corynebacterium glutamicum* S9114ΔnagA-ΔgamA-Δldh, to obtain the genetically engineered strain.

6. A method of producing N-acetylglucosamine comprising:

providing the genetically engineered strain according to claim 2; and producing N-acetylglucosamine from the genetically engineered strain.

7. The method according to claim 6, wherein the genetically engineered strain is inoculated into a fermentation medium, and subjected to aerated fermentation for 72-100 h at 28-30° C.

8. The method according to claim 7, wherein the fermentation medium comprises 90-110 g/L of glucose, 8-12 g/L of corn steep liquor, 0.8-1.2 g/L of $KH_2PO_4$, 18-22 g/L of $(NH_4)_2SO_4$, 0.4-0.6 g/L of $MgSO_4$, 18-22 g/L of $CaCO_3$ and 0.16-0.20 g/L of $FeSO_4$.

* * * * *

SEQUENCE LISTING

```
<160> NUMBER OF SEQ ID NOS: 10

<210> SEQ ID NO 1
<211> LENGTH: 846
<212> TYPE: DNA
<213> ORGANISM: Artificial sequence
<220> FEATURE:
<223> OTHER INFORMATION: Parent RamA transcription factor

<400> SEQUENCE: 1
gtggataccc agcggattaa agatgacgaa gatgctattc gttcggcgct gacatcgctg      60
aaaaccgcaa caggcatccc agtcaccatg ttcgccactg tgttgcagga caatcgcctg     120
caaattactc agtgggttgg gttgcgtacc ccggctctgc agaatctggt cattgaacca     180
ggtgtgggcg ttggtggacg cgtcgtcgca acccgtcgtc cggttggtgt gagtgattac     240
accagggcaa atgtcatttc acatgagaag gattccgcga ttcaggatga gggccttcat     300
tccattgtcg cagttcccgt gatcgtgcac cgcgaaatcc gtggcgtttt gtatgttggc     360
gttcactctg cggtgcgtct cggcgacact gttattgaag aagtcaccat gactgcgcgc     420
acgttggaac aaaacctggc gatcaactcc gcgcttcgcc gcaatggcgt tcctgatggt     480
cgcggttccc tcaaagctaa ccgcgtgatg aatggggcgg agtgggagca ggttcgttcc     540
actcattcca agctgcgcat gctggcaaat cgtgtgaccg atgaggatct gcgtcgcgat     600
ttggaagagc tttgcgatca gatggtcacc ccagtccgca tcaagcagac caccaagctg     660
tccgcgcgtg agttggacgt gctggcttgt gtcgcgctcg gtcacaccaa cgtcgaagct     720
gctgaagaga tgggcatcgg cgcggaaacc gtcaagagct acctgcgctc ggtcatgcgc     780
aagctcggcg cccacacgcg ctacgaggca gtcaacgcag cacgccggat cggcgcactg     840
ccttaa                                                                846

<210> SEQ ID NO 2
<211> LENGTH: 281
<212> TYPE: PRT
<213> ORGANISM: Artificial sequence
<220> FEATURE:
<223> OTHER INFORMATION: Parent RamA transcription factor

<400> SEQUENCE: 2
```

```
Met Asp Thr Gln Arg Ile Lys Asp Asp Glu Asp Ala Ile Arg Ser Ala
1               5                   10                  15
Leu Thr Ser Leu Lys Thr Ala Thr Gly Ile Pro Val Thr Met Phe Ala
            20                  25                  30
Thr Val Leu Gln Asp Asn Arg Leu Gln Ile Thr Gln Trp Val Gly Leu
        35                  40                  45
Arg Thr Pro Ala Leu Gln Asn Leu Val Ile Glu Pro Gly Val Gly Val
    50                  55                  60
Gly Gly Arg Val Val Ala Thr Arg Arg Pro Gly Val Ser Asp Tyr
65                  70                  75                  80
Thr Arg Ala Asn Val Ile Ser His Glu Lys Asp Ser Ala Ile Gln Asp
                85                  90                  95
Glu Gly Leu His Ser Ile Val Ala Val Pro Val Ile Val His Arg Glu
            100                 105                 110
Ile Arg Gly Val Leu Tyr Val Gly Val His Ser Ala Val Arg Leu Gly
        115                 120                 125
Asp Thr Val Ile Glu Glu Val Thr Met Thr Ala Arg Thr Leu Glu Gln
    130                 135                 140
Asn Leu Ala Ile Asn Ser Ala Leu Arg Arg Asn Gly Val Pro Asp Gly
145                 150                 155                 160
Arg Gly Ser Leu Lys Ala Asn Arg Val Met Asn Gly Ala Glu Trp Glu
                165                 170                 175
Gln Val Arg Ser Thr His Ser Lys Leu Arg Met Leu Ala Asn Arg Val
            180                 185                 190
Thr Asp Glu Asp Leu Arg Arg Asp Leu Glu Glu Leu Cys Asp Gln Met
        195                 200                 205
Val Thr Pro Val Arg Ile Lys Gln Thr Thr Lys Leu Ser Ala Arg Glu
    210                 215                 220
Leu Asp Val Leu Ala Cys Val Ala Leu Gly His Thr Asn Val Glu Ala
225                 230                 235                 240
Ala Glu Glu Met Gly Ile Gly Ala Glu Thr Val Lys Ser Tyr Leu Arg
                245                 250                 255
Ser Val Met Arg Lys Leu Gly Ala His Thr Arg Tyr Glu Ala Val Asn
            260                 265                 270
Ala Ala Arg Arg Ile Gly Ala Leu Pro
        275                 280

<210> SEQ ID NO 3
<211> LENGTH: 846
<212> TYPE: DNA
<213> ORGANISM: Artificial sequence
<220> FEATURE:
<223> OTHER INFORMATION: RamA transcription factor mutant

<400> SEQUENCE: 3
gtggataccc agcggattaa agatgacgaa gatgctattc gttcggcgct gacatcgctg      60
aaaaccgcaa caggcatccc agtcaccatg ttcgccactg tgttgcagga caatcgcctg     120
caaattactc agtgggttgg gttgcgtacc ccggctctgc agaatctggt cattgaacca     180
ggtgtgggcg ttggtggacg cgtcgtcgca accgtcgtc cggttggtgt gagtgattac      240
accagggcaa atgtcatttc acatgagaat gataaggcga ttcaggatga gggccttcat     300
tccattgtcg cagttcccgt gatcgtgcac cgcgaaatcc gtggcgtttt gtatgttggc     360
gttcactctg cggtgcgtct cggcgacact gttattgaag aagtcaccat gactgcgcgc     420
acgttggaac aaaacctggc gatcaactcc gcgcttcgcc gcaatggcgt tcctgatggt     480
```

```
cgcggttccc tcaaagctaa ccgcgtgatg aatggggcgg agtgggagca ggttcgttcc    540
actcattcca agctgcgcat gctggcaaat cgtgtgaccg atgaggatct gcgtcgcgat    600
ttggaagagc tttgcgatca gatggtcacc ccagtccgca tcaagcagac caccaagctg    660
tccgcgcgtg agttggacgt gctggcttgt gtcgcgctcg gtcacaccaa cgtcgaagct    720
gctgaagaga tgggcatcgg cgcggaaacc gtcaagagct acctgcgctc ggtcatgcgc    780
aagctcggcg cccacacgcg ctacgaggca gtcaacgcag cacgccggat cggcgcactg    840
ccttaa                                                                846
```

<210> SEQ ID NO 4
<211> LENGTH: 281
<212> TYPE: PRT
<213> ORGANISM: Artificial sequence
<220> FEATURE:
<223> OTHER INFORMATION: RamA transcription factor mutant
<400> SEQUENCE: 4

```
Met Asp Thr Gln Arg Ile Lys Asp Asp Glu Asp Ala Ile Arg Ser Ala
1               5                   10                  15

Leu Thr Ser Leu Lys Thr Ala Thr Gly Ile Pro Val Thr Met Phe Ala
            20                  25                  30

Thr Val Leu Gln Asp Asn Arg Leu Gln Ile Thr Gln Trp Val Gly Leu
        35                  40                  45

Arg Thr Pro Ala Leu Gln Asn Leu Val Ile Glu Pro Gly Val Gly Val
    50                  55                  60

Gly Gly Arg Val Val Ala Thr Arg Arg Pro Gly Val Ser Asp Tyr
65                  70                  75                  80

Thr Arg Ala Asn Val Ile Ser His Glu Asn Asp Lys Ala Ile Gln Asp
                85                  90                  95

Glu Gly Leu His Ser Ile Val Ala Val Pro Val Ile Val His Arg Glu
            100                 105                 110

Ile Arg Gly Val Leu Tyr Val Gly Val His Ser Ala Val Arg Leu Gly
        115                 120                 125

Asp Thr Val Ile Glu Glu Val Thr Met Thr Ala Arg Thr Leu Glu Gln
    130                 135                 140

Asn Leu Ala Ile Asn Ser Ala Leu Arg Arg Asn Gly Val Pro Asp Gly
145                 150                 155                 160

Arg Gly Ser Leu Lys Ala Asn Arg Val Met Asn Gly Ala Glu Trp Glu
                165                 170                 175

Gln Val Arg Ser Thr His Ser Lys Leu Arg Met Leu Ala Asn Arg Val
            180                 185                 190

Thr Asp Glu Asp Leu Arg Arg Asp Leu Glu Glu Leu Cys Asp Gln Met
        195                 200                 205

Val Thr Pro Val Arg Ile Lys Gln Thr Thr Lys Leu Ser Ala Arg Glu
    210                 215                 220

Leu Asp Val Leu Ala Cys Val Ala Leu Gly His Thr Asn Val Glu Ala
225                 230                 235                 240

Ala Glu Glu Met Gly Ile Gly Ala Glu Thr Val Lys Ser Tyr Leu Arg
                245                 250                 255

Ser Val Met Arg Lys Leu Gly Ala His Thr Arg Tyr Glu Ala Val Asn
            260                 265                 270

Ala Ala Arg Arg Ile Gly Ala Leu Pro
        275                 280
```

<210> SEQ ID NO 5
<211> LENGTH: 26
<212> TYPE: DNA
<213> ORGANISM: Artificial sequence
<220> FEATURE:
<223> OTHER INFORMATION: Upstream primer FragmentRamA.FOR

<400> SEQUENCE: 5
cgtcgaataa gacgcgccct atgggt                                          26

<210> SEQ ID NO 6
<211> LENGTH: 29
<212> TYPE: DNA
<213> ORGANISM: Artificial sequence
<220> FEATURE:
<223> OTHER INFORMATION: Downstream primer FragmentRamA.REV

<400> SEQUENCE: 6
cctttgctag tttaaggcag tgcgccgat                                       29

<210> SEQ ID NO 7
<211> LENGTH: 37
<212> TYPE: DNA
<213> ORGANISM: Artificial sequence
<220> FEATURE:
<223> OTHER INFORMATION: Upstream primer VectorRamA.FOR

<400> SEQUENCE: 7
cactgcctta aactagcaaa ggagaagaaa agccgga                              37

<210> SEQ ID NO 8
<211> LENGTH: 46
<212> TYPE: DNA
<213> ORGANISM: Artificial sequence
<220> FEATURE:
<223> OTHER INFORMATION: Downstream primer VectorRamA.REV

<400> SEQUENCE: 8
tagggcgcgt cttattcgac ggtgacagac tttgccaggt tacgag                    46

<210> SEQ ID NO 9
<211> LENGTH: 27
<212> TYPE: DNA
<213> ORGANISM: Artificial sequence
<220> FEATURE:
<223> OTHER INFORMATION: Upstream primer RamAM.FOR
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (7)..(9)
<223> OTHER INFORMATION: n is a, c, g, or t

<400> SEQUENCE: 9
nnngatnnng cgattcagga tgagggc                                         27

```
<210> SEQ ID NO 10
<211> LENGTH: 35
<212> TYPE: DNA
<213> ORGANISM: Artificial sequence
<220> FEATURE:
<223> OTHER INFORMATION: Downstream primer RamAM.REV

<400> SEQUENCE: 10
ctcatgtgaa atgacatttg ccctggtgta atcac                              35
```